United States Patent
Yoshitome et al.

(10) Patent No.: US 8,124,144 B2
(45) Date of Patent: Feb. 28, 2012

(54) METHOD OF PRODUCING BLOOD TYPE CHECKING REAGENT CONTAINING LECTIN

(75) Inventors: Shokichi Yoshitome, Miyazaki (JP); Shinichi Tanimura, Miyazaki (JP); Tomomi Taniguchi, Miyazaki (JP); Ryo Akashi, Miyazaki (JP)

(73) Assignee: Oki Semiconductor Co., Ltd., Tokyo (JP)

( * ) Notice: Subject to any disclaimer, the term of this patent is extended or adjusted under 35 U.S.C. 154(b) by 541 days.

(21) Appl. No.: 12/292,503

(22) Filed: Nov. 20, 2008

(65) Prior Publication Data

US 2009/0092694 A1 Apr. 9, 2009

Related U.S. Application Data

(60) Continuation of application No. 12/068,474, filed on Feb. 7, 2008, now abandoned, which is a division of application No. 11/253,667, filed on Oct. 20, 2005, now abandoned.

(30) Foreign Application Priority Data

Oct. 29, 2004 (JP) .................................. 2004-315366

(51) Int. Cl.
*A61K 36/00* (2006.01)
(52) U.S. Cl. ........................................ 424/776; 424/725
(58) Field of Classification Search ........................ None
See application file for complete search history.

(56) References Cited

FOREIGN PATENT DOCUMENTS

JP 11-083862 3/1999
JP 2001-056341 2/2001

OTHER PUBLICATIONS

"Antibody Dilution Buffers". Internet Archive Date: Aug. 10, 2004. [Retrieved from the Internet on: Mar. 28, 2011]. Retrieved from the Internet: <URL: http://replay.waybackmachine.org/20040810115042/http://www.ihcworld.com/_protocols/antibody_diluents/ab_dilution_buffer.htm>.*
Barbieri L., et al. "Inhibition of Protein Synthesis in vitro by Proteins from the Seeds of *Momordica charantia* (Bitter Pear Melon)". Biochemical Journal, vol. 186, (1980) 443-452.

\* cited by examiner

*Primary Examiner* — Amy L Clark
(74) *Attorney, Agent, or Firm* — Kubotera & Associates, LLC

(57) ABSTRACT

Lectin is extracted from seeds of bitter gourd (also known as balsam pear or *Momordica charantia*). A blood type checking reagent for checking a blood type includes the lectin. The lectin extracted from seeds of bitter gourd preferably has a molecular weight between 100,000 and 170,000 measured with polyacrylamide gel electrophoresis in existence of sodium dodecyl sulfate (SDS-PAGE). A method of checking a blood type includes the steps of: extracting lectin from seeds of bitter gourd (also known as balsam pear or *Momordica charantia*); preparing a blood type checking reagent containing the lectin; and checking a blood type using the blood type checking reagent.

2 Claims, No Drawings

METHOD OF PRODUCING BLOOD TYPE CHECKING REAGENT CONTAINING LECTIN

CROSS-REFERENCE TO RELATED APPLICATIONS

This is a continuation application of the prior application No. 12/068,474 filed Feb. 7, 2008 now abandoned, pending, which is a divisional application of the prior application Ser. No. 11/253,667 filed Oct. 20, 2005, abandoned. The disclosure of Japanese Patent Application No. 2004-315366, filed on Oct. 29, 2004, is incorporated in the application by reference.

BACKGROUND OF THE INVENTION AND RELATED ART STATEMENT

The present invention relates to a method of producing a blood type checking reagent containing a lectin. The blood type checking reagent exhibits specific cohesion relative to H-antigen on a red blood cell membrane or an erythrocyte membrane. Accordingly, it is possible to accurately and quickly determine a blood type even from a small bloodstain.

In general, lectin extracted from a plant includes anti-A1 lectin (from *Dolicos biflorus*) and anti-H lectin (from *Ulex europaeus*). The anti-H lectin extracted from *Ulex europaeus* has been used for, for example, determining a blood type. Anti-H lectin with improved activity is called H-antigen lectin strong, and suitable for checking a blood type of a trace amount of body fluid and a hair (dissociation test). The anti-H lectin strong has agglutinin tilter four times larger than that of conventional anti-H lectin. Accordingly, it is possible to determine a blood type of a small amount of sample (refer to Non-patent Reference 1 and Non-patent Reference 2). The following table shows comparison of agglutinin tilter between the anti-H lectin strong and the conventional anti-H lectin.

|  | Agglutinin tilter* |
|---|---|
| Anti-H lectin | $2^6$ (64) |
| Anti-H lectin strong | $2^8$ (256) |

*Measured with continuous dilution method (2% O-type human erythrocyte agglutinin tilter PBS)

Further, lectin may be extracted from animal such as loach, especially from an egg thereof. The lectin extracted from loach has a molecular weight of 15,000 to 50,000, and is used for determining a blood type (refer to Patent Reference 1).

Non-patent Reference 1: Japanese Society of Laboratory Medicine Library XII (1996)
Non-patent Reference 2: Product Report No. 105 (Seikagaku Corporation)
Patent Reference 1: Japanese Patent Publication No. 11-083862

The conventional method of checking a blood type has the following disadvantages. First, it is difficult to determine a blood type sampled from a bloodstain (dissociation test) using the anti-H lectin extracted from *Ulex europaeus*. Second, it is difficult to obtain raw materials for producing the blood type checking reagent using the conventional anti-H lectin. Further, it is necessary to use a large amount of raw materials, thereby increasing cost. Third, the agglutinin tilter of the lectin extracted from *Ulex europaeus* largely depends on a raw material (seed), and it is difficult to obtain constant agglutinin tilter within lot. Fourth, it is difficult to detect H-antigen using the lectin extracted from loach.

In view of the problems described above, an object of the present invention is to provide lectin for checking a blood type and a blood type checking reagent containing the lectin, in which it is possible to accurately and quickly determine a blood type even from a small bloodstain. Another object of the present invention is to provide a method of checking a blood type using the blood type checking reagent containing the lectin.

Further objects and advantages of the invention will be apparent from the following description of the invention.

SUMMARY OF THE INVENTION

In order to attain the objects described above, according to the present invention, lectin for checking a blood type is extracted from seeds of bitter gourd (also known as balsam pear or *Momordica charantia*). According to the present invention, a blood type checking reagent contains the lectin. The lectin extracted from seeds of bitter gourd preferably has a molecular weight between 100,000 and 170,000 measured with poly-acrylamide gel electrophoresis in existence of sodium dodecyl sulfate (SDS-PAGE).

According to the present invention, a method of checking a blood type includes the steps of: extracting lectin from seeds of bitter gourd (also known as balsam pear or *Momordica charantia*); preparing a blood type checking reagent containing the lectin; and checking a blood type using the blood type checking reagent.

With the blood type checking reagent containing the anti-H lectin of the present invention, it is possible to accurately and quickly determine a blood type even from a small bloodstain.

In the present invention, the blood type checking reagent includes the lectin having high agglutinin tilter and extracted from seeds bitter gourd, i.e., a low cost raw material. In general, after removing flesh from bitter gourd, seeds are usually disposed or used for feeding animals. Therefore, cost of the low material is very low. Further, it is possible to extract and refine the lectin with cost same as that of conventional lectin. Accordingly, it is possible to produce the lectin with low cost as compared with conventional lectin for checking a blood type.

Further, as compared with conventional lectin, the lectin extracted from seeds of bitter gourd blood exhibits a specific agglutination reaction or hemagglutination relative to H-antigen and high agglutinin tilter. Accordingly, it is possible to accurately and quickly determine a blood type even from a small bloodstain, thereby obtaining reliable data for forensic investigation. Due to the high agglutinin tilter, the lectin extracted from seeds of bitter gourd shows stable agglutinin tilter within lot with little influence of raw materials.

DETAILED DESCRIPTION OF PREFERRED EMBODIMENTS

Hereunder, embodiments of the present invention will be explained with reference to the accompanying drawings. The explanation covers seeds of bitter gourd, extraction and refinement of lectin, a range of molecular weight, blood type determination, a blood type checking reagent, and an elution test of bloodstain.

According to the present invention, a type of bitter gourd is not limited to a specific one. It is possible to extract lectin from any types of bitter gourd, and seeds may be fully matured or pre-matured. It is found that matured or ripe seeds provide lectin with higher agglutinin tilter. However, it is possible to obtain the same effect on determining a blood type with matured seeds or pre-matured seeds.

According to the present invention, the lectin preferably has a molecular weight between 100,000 and 170,000. The molecular weight may be measured with poly-acrylamide gel electrophoresis in existence of sodium dodecyl sulfate (SDS-PAGE), in particular, with non-continuous gel electrophoresis (Laemmli method) using a concentrated gel. It is found that the lectin with a molecular weight between 100,000 and 170,000 effectively agglutinates blood. That is, it is difficult to agglutinate blood with lectin having a molecular weight less than 100,000 or larger than 170,000.

An operation of extracting the lectin will be explained next. Dried seeds of bitter gourd, regardless of matured or pre-matured seeds, are used.

1. 10 g of dried bitter gourd seeds were ground in a coffee mill to obtain fine power.
2. The fine powder was added to 100 ml of distilled water, and the mixture was stirred with a stirrer for three hours.
3. The mixture was filtered with a bleached cloth to obtain filtrate.
4. The filtrate was centrifuged with a centrifuge for 10 minutes at 5000 rpm to obtain supernatant.
5. 150 ml (1.5 times of the distill water added in step 2) of ethanol was added to the supernatant, and the mixture was stirred and placed still for one hour.
6. Supernatant of the mixture was removed to obtain deposit, and the deposit was centrifuged with a centrifuge for 10 minutes at 5000 rpm.
7. Supernatant was removed to obtain deposit, and the deposit was spread on an evaporating dish to be dried.
8. The dried deposit was collected and ground with a mortar to obtain powder (about 0.3 g). The powder was added to 5 to 10 ml of normal saline solution containing gelatin to obtain solution.
9. The solution was centrifuged with a centrifuge for 10 minutes at 5000 rpm to obtain supernatant as anti-H lectin.

A method of measuring agglutinin tilter of the lectin thus obtained will be explained next.

1. Serum was diluted double with normal saline solution, and divided into test tubes by 0.25 ml each.
2. O-type blood cells corresponding to the anti-H lectin washed with normal saline solution three times to obtain 2% normal saline solution suspension. 0.25 ml of the normal saline solution suspension was added to the diluted serum in a test tube to obtain a mixture. The test tube was then rigorously shaken.
3. The mixture was centrifuged with a centrifuge for 1 minute at 1000 rpm.
4. The test tube was gently shaken to observe hemagglutination.
5. An extent of hemagglutination was classified from 1 to 3. Maximum dilution number of a test tube showing hemagglutination of 1 is designated as agglutinin tilter of the serum.

The extent of hemagglutination is measured relative to various types of blood (refer to Table 4). For example, agglutinin tilter of O-type blood measured with anti-H lectin extracted from seeds of bitter gourd was found to be $2^8$ (256) times with a hole-glass method (after placed in a room temperature for 30 minutes) or $2^9$ (512) times with the test tube method (after centrifuged for 1 minute at 1000 rpm). The method of measuring agglutinin tilter is disclosed in "forensic serology test manual", 90 page, table 3-12 (Published by Kinbara Shuppan).

A process of dissociation test and evaluating an agglutination reaction will be explained next. When a bloodstain is attached to a piece of metal, a stone, a piece of plastic, or a piece of fiber, a cotton fiber or a small gauze dampened with distilled water is rubbed against a location of the bloodstain, so that the bloodstain is stick to the cotton fiber or the gauze as a test specimen. Alternatively, the bloodstain is stick to a small amount of fibers solved in a solution, and the fibers are dried to obtain a test specimen. When it is difficult to cut out a portion with a bloodstain, or a bloodstain is stick to powder or a block, the same procedure is applied to obtain a test specimen.

After obtaining a test specimen, a method described in "forensic serology test manual", 181 page, table 4-22 (Published by Kinbara Shuppan) is performed. The method has been frequently used in forensic investigation due to simplicity and high sensitivity. Apparatus and reagents used in the method include an environmental bath (Constant temperature bath LT-480 manufactured by ADVENTEC), test tubes, hole glasses, anti-A serum, anti-B serum, anti-H lectin, respirator, and blood cell indicator.

1. A portion of a sample with bloodstain or a target portion was cut out in about 1.5 cm square, and divided into three pieces.
2. Each of the three pieces was placed in a test tube with a specimen name (bloodstain, control) and a name of agglutinin (anti-H, anti-A, anti-B).
3. 0.1 ml of agglutinin was added to the test tube with a corresponding label. Anti-H lectin was used as the anti-H agglutinin.
4. The agglutinin absorbed a blood sample.
5. After absorbing the blood sample, cold normal saline solution was poured into the test tube in full. Then, normal saline solution containing un-reacted antibody was removed while the specimen remained in the test tube.
6. The specimen dampened with normal saline solution in the test tube was divided into three portions. 0.2% erythrocyte suspension of O-type, A-type, or B-type was added to each of the three portions, and mixtures were heated at 56° C. for 10 minutes (dissociation).
7. The test tube was centrifuged with a centrifuge for 1 minute at 1000 rpm.

A method of evaluating an agglutination reaction or hemagglutination is performed as follows with reference to "forensic serology test manual", 181 page, table 4-22 (Published by Kinbara Shuppan). After being centrifuged, the test tube is gently shaken, and the result is evaluated based on an evaluation table. In this case, the results of hemagglutination are compared between the anti-H lectin from Ulex and the anti-H lectin from bitter gourd.

In the embodiment, the anti-H lectin is extracted from seeds of bitter gourd (balsam pear, or *Momordica charantia*), and is formed of a hemagglutination protein. Accordingly, in a case of Para-Bombay-type blood, the anti-H lectin does not exhibit hemagglutination, indicating that the lectin from bitter gourd is an anti-H type.

A process of extracting the lectin from bitter gourd will be explained next.

1. 100 g of seeds of bitter gourd were ground in a coffee mill to obtain powder.
2. The powder was added to one litter of distilled water in a container, and the mixture was stirred with a stirrer.
3. The mixture was placed still for more than 12 hours to extract seed components of bitter gourd.
4. The mixture was filtered with a bleached cloth to obtain extracted solution.
5. The extracted solution was centrifuged with a centrifuge for 30 minutes at 3000 rpm to obtain supernatant.
6. After being centrifuged, approximately two litters of ethanol was added to the supernatant, and the mixture was stirred and placed still for 12 hours at 4° C. for incubation.

Through the steps described above, it is possible to extract crude anti-H lectin. Although the crude anti-H lectin contains lectin, other proteins, and sugar, it is found that the crude anti-H lectin exhibits sufficient agglutinin tilter.

A process of refining the crude anti-H lectin thus obtained will be explained next.
1. Supernatant of the extracted fluid was removed with an aspirator to obtain deposit.
2. The deposit was centrifuged with a centrifuge for 30 minutes at 3000 rpm to separate a liquid portion.
3. The deposit was spread in a wide mouth container and dried to obtain a dried product.
4. The dried product was solved in 100 ml of normal saline solution containing gelatin to obtain solution.
5. The solution was centrifuged with a centrifuge for 30 minutes at 3000 rpm to obtain supernatant.

Through the steps described above, it is possible to obtain refined anti-H lectin. The lectin thud refined has a molecular weight of about 120,000 measured with the SDS-PAGE method. The anti-H lectin thus refined contains a less amount of other proteins and sugar, and has a higher purity and agglutinin tilter.

An experiment of determining a blood type using a blood type checking reagent containing the lectin extracted from bitter gourd described above will be explained next. The experiment includes a test of determining a type of a blood cell through hemagglutination (chart test or absorption-elution test) using the anti-H lectin extracted from bitter gourd; a dissociation test of an ABO type blood test of bloodstain using the anti-H lectin extracted from bitter gourd; and a dissociation test of an Para-Bombay-type blood test of bloodstain using the anti-H lectin extracted from bitter gourd through the method described above.

Results of the tests using 50 μl of the lectin are shown in the following Table 1 to Table 3.

TABLE 1

Chart test using the bitter gourd anti-H lectin

| Chart Test Result | Bitter gourd lectin (agglutinin tilter x32) | Bitter gourd lectin (agglutinin tilter x64) | Bitter gourd lectin (agglutinin tilter x128) |
| --- | --- | --- | --- |
| Para-Bombay-type blood cell (no H-antigen) | — | ‡* | ‡* |
| O-type blood cell | 3 | 3 | 3 |

‡* abnormal hemagglutination due to excess antigen

TABLE 2

Dissociation test of the ABO type blood test of a bloodstain using the bitter gourd anti-H lectin

| Specimen | Anti-A antigen (α) | Anti-B antigen (β) | Ulex lectin (agglutinin tilter × 32) | Bitter gourd lectin (agglutinin tilter × 32) | Bitter gourd lectin (agglutinin tilter × 64) | Bitter gourd lectin (agglutinin tilter × 128) |
| --- | --- | --- | --- | --- | --- | --- |
| A-type blood cell | 2 | — | —* | — | 1 | 2 |
| A-type blood cell | — | 2 | —* | ‡ | 2 | 3 |
| A-type blood cell | — | — | —* | ‡ | 2 | 3 |

*Undetectable with the anti-H lectin extracted from Ulex seeds

TABLE 3

Dissociation test of a bloodstain using the bitter gourd anti-H lectin

| Specimen | Time | Bitter gourd lectin | | | | | |
| --- | --- | --- | --- | --- | --- | --- | --- |
| | | X32 | X64 | X128 | X256 | X512 | X1024 |
| A-type bloodstain | 10 | ‡ | 1 | 1 | 1 | 1 | 1 |
| A-type bloodstain | 10 | 1 | 2 | 2 | 2 | 2 | 2 |
| Para-Bombay bloodstain | 10 | — | — | — | — | — | — |
| A-type bloodstain | 15 | ‡ | 2 | 2 | 2 | 2 | 2 |
| A-type bloodstain | 15 | 2 | 3 | 3 | 3 | 3 | 3 |
| Para-Bombay bloodstain | 15 | — | — | — | — | — | — |
| A-type bloodstain | 20 | ‡ | 2 | 2 | 2 | 2 | 2 |
| A-type bloodstain | 20 | 2 | 3 | 3 | 3 | 3 | 3 |
| Para-Bombay bloodstain | 20 | — | — | — | — | — | — |
| Para-Bombay bloodstain | 30 | — | — | — | — | — | — |

As shown in Table 1 to Table 3, the blood checking reagent containing the anti-H lectin extracted from bitter gourd exhibited high reactivity relative to a bloodstain, while the conventional Ulex lectin did not detect. Accordingly, the blood checking reagent of the present invention is superior to the conventional reagent in terms of agglutinin tilter and hemagglutination.

Results of an evaluation of the blood checking reagent of the present invention will be explained with reference to Table 4 to Table 8.

TABLE 4

Agglutinin tilter relative to various blood cells

| Agglutinin | Blood cell (2% suspension) | Agglutinin tilter Hole glass method (1) | Test tube method (2) |
|---|---|---|---|
| Anti-H lectin extracted from seeds of bitter gourd | O-type blood cell | $2^8$ (256) | $2^9$ (512) |
| | $A_1$-type blood cell | $2^6$ (64) | $2^7$ (128) |
| | $A_2$-type blood cell | $2^8$ (256) | $2^9$ (512) |
| | B-type blood cell | $2^6$ (64) | $2^7$ (128) |

(1) Evaluate at room temperature for 30 minutes
(2) Centrifuged at 1000 rpm for 1 minutes

TABLE 5

Agglutinin tilter (chart test: mixed on a flat glass plate)

| Blood cell (2% suspension) | Anti-H lectin extracted from seeds of bitter gourd | Anti-H lectin extracted from seeds of Ulex |
|---|---|---|
| O-type blood cell | Ca. 20 seconds | Ca. 2 minutes |
| $A_1$-type blood cell | Ca. 35 seconds | Ca. 15 minutes |
| $A_2$-type blood cell | Ca. 25 seconds | Ca. 2 minutes |
| B-type blood cell | Ca. 35 seconds | Ca. 15 minutes |
| Para-Bombay-type blood cell | No hemagglutination | No hemagglutination |

As shown in Table 5, the conventional anti-H lectin extracted from seeds of Ulex took 2 to 15 minutes for hemagglutination. On the other hand, the anti-H lectin extracted from seeds of bitter gourd took few tens of seconds for hemagglutination, indicating high reactivity. Para-Bombay-type blood cell, occurring one out of million people, did not show hemagglutination, indicating the lectin extracted from seeds of bitter gourd is the anti-H lectin.

TABLE 6

Storage stability (relative to O-type blood cell)
Lot. No. GL4917-1

| Storage temperature | Storage time | Agglutinin tilter |
|---|---|---|
| 20° C. | 3 months | $2^8$ (256) |
| 4° C. | 3 months | $2^8$ (256) |
| −30° C. | 3 months | $2^8$ (256) |
| −80° C. | 3 months | $2^8$ (256) |

As shown in Table 6, when the anti-H lectin was stored for 3 months, temperature did not affect the stability of agglutinin tilter.

TABLE 7

Stability during heating (relative to O-type blood cell)

| Heating temperature | Storage time | Agglutinin tilter |
|---|---|---|
| 37° C. | 60 minutes | $2^8$ (256) |
| 55° C. | 10 minutes | $2^8$ (256) |
| 56° C. | 30 minutes | $2^7$ (128) |
| 60° C. | 10 minutes | $2^7$ (128) |
| 70° C. | 10 minutes | $2^3$ (8) |

As shown in Table 7, when the anti-H lectin was heated, high agglutinin tilter (256) was maintained up to 55° C.

TABLE 8

Dissociation test of various blood types of bloodstains
(bloodstains on cotton fibers: evaluated with 0.3% human blood cell)

| Bloodstain | Anti-A antigen (α) | Anti-B antigen (β) | Bitter gourd lectin | Ulex lectin |
|---|---|---|---|---|
| A-type bloodstain | 2 | — | 2 | — |
| B-type bloodstain | — | 2 | 3 | — |
| O-type bloodstain | — | — | 3 | — |
| Para-Bombay-type bloodstain | — | — | — | — |

As shown in Table 8, it is possible to determine A-type bloodstain with anti-A antigen and the bitter gourd lectin (anti-H antigen), and B-type bloodstain with anti-B antigen and the bitter gourd lectin (anti-H antigen). Further, it is not possible to determine O-type bloodstain with anti-A antigen, anti-B antigen, and the conventional Ulex lectin. Accordingly, the blood checking reagent containing the anti-H lectin extracted from bitter gourd exhibited high reactivity in terms of agglutinin tilter and hemagglutination, and was superior to the conventional reagent.

TABLE 9

Comparison of agglutinin tilter between the bitter gourd anti-H lectin and commercially available anti-H lectin (relative to O-type blood cell)

| Agglutinin | | Manufacture | Price (Japanese Yen) | Agglutinin tilter Hole glass method (1) | Test tube method (2) |
|---|---|---|---|---|---|
| Bitter gourd lectin | | | | $2^8$ (256) | $2^9$ (512) |
| Ulex lectin | Anti-H lectin (8 ml) | Honen Corp. | 10,000 | $2^6$ (64) | $2^7$ (128) |
| | Anti-H lectin strong (2 ml) | Honen Corp. | 10,000 | $2^8$ (256) | $2^9$ (512) |
| | Anti-H lectin (3 ml) | Wako Pure Chemical | 10,000 | $2^3$ (8) | $2^4$ (16) |
| | Anti-H lectin (2 ml) | EY Laboratory | 10,000 | $2^3$ (8) | $2^4$ (16) |

(1) Evaluate at room temperature for 30 minutes
(2) Centrifuged at 1000 rpm for 1 minutes As shown in Table 9, the blood checking reagent containing the anti-H lectin extracted from bitter gourd exhibited high agglutinin tilter as compared with the conventional reagents containing Ulex lectin.

While the invention has been explained with reference to the specific embodiments of the invention, the explanation is illustrative and the invention is limited only by the appended claims.

What is claimed is:
1. A method of making a purified anti-H lecithin, comprising the steps of:
   grinding seeds of bitter gourd to obtain a first powder;
   adding the first powder to distilled water followed by stirring for three hours to obtain a first mixture;
   filtering the first mixture to obtain a filtrate;

centrifuging the filtrate to obtain a first supernatant;
adding the first supernatant to ethanol followed by stirring, then left to stand for one hour to obtain a second mixture;
removing a second supernatant of the second mixture to obtain a first deposit;
centrifuging the first deposit to obtain a second deposit;
drying the second deposit to obtain a second powder;
adding the second powder to a normal saline solution containing gelatin to obtain a third mixture;
centrifuging the third mixture to obtain the purified anti-H lecithin, wherein the purified anti-H lecithin is used as a blood type checking reagent.

2. The method of claim 1, wherein said lectin has a molecular weight between 100,000 and 170,000 as measured with poly-acrylamide gel electrophoresis in the presence of sodium dodecyl sulfate (SDS-PAGE).

* * * * *